United States Patent [19]

Schwengers

[11] Patent Number: 4,649,058
[45] Date of Patent: Mar. 10, 1987

[54] GLUCO-OLIGOSACCHARIDE MIXTURE AND A PROCESS FOR ITS MANUFACTURE

[75] Inventor: Dieter Schwengers, Dormagen, Fed. Rep. of Germany

[73] Assignee: Pfeifer & Langen, Cologne, Fed. Rep. of Germany

[21] Appl. No.: 741,394

[22] Filed: Jun. 5, 1985

[30] Foreign Application Priority Data

Jun. 15, 1984 [DE] Fed. Rep. of Germany ....... 3422247

[51] Int. Cl.⁴ .................. C12D 13/02; A23L 1/236
[52] U.S. Cl. ..................................... 426/658; 435/96; 435/97; 435/78; 435/99; 426/804
[58] Field of Search .............. 435/97, 96, 78, 99; 426/658, 548, 804, 661, 52

[56] References Cited

U.S. PATENT DOCUMENTS

| | | | |
|---|---|---|---|
| 3,652,398 | 3/1972 | Armbruster et al. | 435/97 |
| 3,701,714 | 10/1972 | Okada et al. | 435/97 |
| 3,703,440 | 11/1972 | Okada et al. | 435/97 |
| 3,819,484 | 6/1974 | Okada et al. | 435/97 |
| 3,923,598 | 12/1975 | Horikoshi et al. | 435/97 |
| 4,135,977 | 1/1979 | Horikoshi et al. | 435/97 |
| 4,219,571 | 8/1980 | Miyake | 435/97 |
| 4,254,227 | 3/1981 | Okada et al. | 435/97 |
| 4,477,568 | 10/1984 | Hokse et al. | 435/97 |

FOREIGN PATENT DOCUMENTS

| | | | |
|---|---|---|---|
| 0164656 | 12/1985 | European Pat. Off. | 435/97 |
| 0164655 | 12/1985 | European Pat. Off. | 435/97 |
| 0227269 | 12/1984 | Japan | 435/97 |

*Primary Examiner*—Jeanette Hunter
*Attorney, Agent, or Firm*—Sprung Horn Kramer & Woods

[57] ABSTRACT

A gluco-oligosaccharide mixture having up to 30, in particular from 10 to 20, anhydroglucose units is prepared by reacting an aqueous solution of a mono-or disaccharide composed of glucose units containing more than 200 mmol of the saccharide per 1000 U $\alpha(1\rightarrow6)$-D-glucosyl transferase, at 265 to 310 K and a pH value of from 4.5 to 8.0, with an aqueous solution of sucrose in a molar ratio of sucrose to glucose of 2.0 to 5.0.

The oligosaccharide mixtures of the present invention are used as calorie-free carrier for sweetening agents and as "body building" sweetening agent.

18 Claims, No Drawings

GLUCO-OLIGOSACCHARIDE MIXTURE AND A PROCESS FOR ITS MANUFACTURE

Low calorie sweetening agents or those consisting of a carbohydrate carrier and conventional sweetening agents, such as saccharinose, zyklamat or acesulfam-K are already prior art.

The invention relates to sweetening agents of the kind and to carriers in the form of an iso-malto-oligosaccharide mixture having up to 30, in particular from 10 to 20, anhydroglucose units. To date, these oligosaccharides were obtained only as waste product in the preparation of clinical dextrans by acid hydrolysis of high molecular weight native dextrans, however, they had a very broad molecular weight distribution, starting from glucose up to molecular weights of about 50000.

The object of the invention is to synthesize iso-malto-oligosaccharide mixtures having up to 30, in particular from 10 to 20, anhydroglucose units in each of the desirable narrow molecular weight distribution.

This problem is solved by the process of this invention which is characterized by adding to an aqueous solution of a mono- or disaccharide composed of D-glucose units containing, more than 200 mmol D-glucose per 1000 U $\alpha$ (1→6)-D-glucosyl transferase, at 265 to 310 K and a pH value of 4.5 to 8.0 an aqueous solution of sucrose, in such an amount that the mole ratio of sucrose to glucose is from 2.0 to 5.0.

The reaction mixture is preferably maintained at from 290 to 300 K and a pH value in the range of 5 to 6.5. Both parameters have an influence on the structure of the resulting products.

According to the classification of the "Enzyme Commission", enzymes which transfer the D-glucopyranosyl group of sucrose to suitable acceptors are designated as $\alpha$ (1→6)-D-glucosyl transferase. An extracellular enzyme of the kind is dextran sucrase (E.C. 2.4.1.5), which is formed by specific kinds of bacteria of the lactobacilli species, for example, *Leuconostoc mesenteroides*, in particular the strain B-512, *Leuconostoc dextranicum*, Streptococcus and lactobacillus. When preparing dextran, sucrose serves primarily as acceptor and acts as chain initiator for a chain polymerization in which by virtue of continuous transfer of D-glucopyranosyl groups from the sucrose to the growing chain of the polysaccharide, dextrans having molecular masses of several millions are formed, while, at the same time, a fructose molecule is liberated for each reacted molecule of sucrose.

If one uses in this reaction other mono- di- or trisaccarides as acceptor, oligosaccharides are produced to a minor extent at the expense of the dextran. When employing glucose as acceptor, about 78 percent dextran and, as by-product, about 9 percent oligodextran saccharides (IM-3 to IM-12) are produced. With maltose as acceptor other lower oligosaccharides having up to 6 anhydroglucose units and native dextran are obtained. (Robyt and Eklund, Carbohydrate Research 121 (1983) 279–286). Typically, the oligosaccharides are produced in decreasing amounts with increasing degree of polymerization.

It is possible under the reaction conditions of the present invention to control the transfer of glucosyl groups from sucrose to mono- and disaccharides composed of D-glucose units such that no native dextran is produced, but gluco-oligosaccharides having up to 30, particularly 10 to 20 anhydroglucose units are formed in high yield. Surprising is hereby that the gluco-oligosaccharides are no longer formed in decreasing amounts with increasing degree of polymerization, but that, depending on the reacted amount of sucrose, glucooligosaccharides having a specific polymerization degree are preferably formed.

According to the process of this invention, it is recommendable for obtaining a high yield of the desired oligosaccharides to add the aqueous solution of sucrose continuously at such a rate that the amount of enzyme can immediately convert the amount of sucrose being fed thus avoiding an accummulation of sucrose in the reaction mixture which may lead to the uncontrolled formation of high molecular weight dextran. At all events, the sucrose content of the carbohydrate dry substance of the reaction mixture should not exceed 25 percent at the equilibrium condition of the continuous reaction. Instead of the purified dextran-sucrase, also the mixture comprising the enzyme and the bacteria which produce said enzyme may be empolyed. The synthesis may be described as follows.

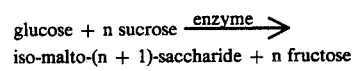

I

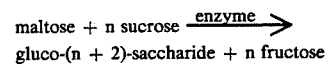

II whereby n represents the number of moles of the sucrose, the glucose units of which serve for forming the oligosaccharide, while a corresponding mole number of fructose is liberated. If n=9, according to I iso-maltodecaose (IM-10) is formed.

This reaction may be controlled according to the invention in such a manner that oligo- or polysaccharides of the desired molecular weight are obtained. Under the specified conditions of temperature and hydrogen ion concentration, the resulting molecular weight depends on the molar amount of the acceptor, based on a specific enzyme activity in the solution, and the mole ratio of the total amount of sucrose added to the acceptor.

The enzyme activity unit U (=Unit) is the amount of the $\alpha$(1→6)-D-glucosyl transferase which converts 1 mmol sucrose per minute at a pH of 5.2 and 298 K. If more sucrose is fed than the present enzyme activity can convert, the control of the size of the molecules will no longer be possible.

If an enzyme activity of 1000 U is taken as basis, the desired oligosaccharide mixture, having an average molecular weight of about 2000 to 5000, will be obtained at an overall sucrose addition of 1000 mmol and of 200 to 500 mmol glucose.

It is thus possible to control in a few preliminary tests with changing molar amounts of glucose within the specified range at predetermined activity of the $\alpha$(1→6)-D-glucosyl transferase (e.g. 1,000 U) and a constant amount of sucrose (e.g. 1,000 mmol), the linkage of the D-glucose pyranosyl groups of the sucrose to the acceptor in such a manner that fractions of each of the desired oligo- or polysaccharides having a narrow molecular weight distribution can be synthesized in high yield.

It is possible to provide the entire necessary amount of glucose, or, while observing the other reaction conditions, in particular the concentration ratios, to replace these saccharides continuously to the extent to which they are consumed as acceptors. It is also possible to conduct the synthesis are a fully continuous reaction.

An unexpected advantage of the process of the invention is that the carbonhydrate content in the dry substance of the reaction mixture may be very high, being as high as 30 to 50 percent, in particular 40 to 50 percent.

Although the enzymatic synthesis according to the invention is carried out under sterile conditions, as is, for example, conventional in the synthesis of native dextran, antimitotics (mytosis inhibitors) may be added to the reaction mixture, such as sulfurous acid, in amounts of up to 1000 mg/kg, in particular 400 to 600 mg/kg, in order to avoid undesired growth of yeast.

If mono- and disaccharides are undesired in the reaction product, depending of its provided use, the oligosaccharides can be separated by precipitation-fractionation or by chromatography.

This product may be utilized as carrier for sweetening agents and as starting product for the preparation of iron dextran.

Subject matter of the invention is, furthermore, a mixture of oligosaccharides having up to 30, in particular from 10 to 20 anhydroglucose units and more fructose than glucose, as is obtained according to the process of the invention. This mixture is particularly suitable as "body building" sweetening agents.

EXAMPLE 1

7.3 kg crystalline glucose were dissolved at 298 K in 16 liters of an aqueous solution of the enzyme dextran sucrase which had an activity of 5400 U/1. The pH value of the solution was 5.4; 2.6 kg/h of a 40 percent-sucrose solution having a pH of 5.4 were continuously pumped into said solution. The addition of the sucrose was terminated after 48 hours and the enzyme was deactivated after 2 further hours by heating the reaction mixture to 70° C.

The mono- and disaccharide components were separated from a sample of the reaction mixture by gel chromatography and the mean value, $M_n$, of the molecular weight of the oligosaccharide fraction was determined by the Somogyi-Phosphate Method (Methods in Carbohydrate Chemistry, Vol. I, (1962), p. 384-386). It was determined to be $M_n=2540$, which corresponds to an average degree of polymerization of 15.7 anhydroglycose units.

The fructose content in the carbohydrate dry substance was 45.0 percent, the glucose content 3.6 percent.

EXAMPLE 2

Iso-malto-oligosaccharide mixture as carrier for sweetening agents 7.1 grams of the sweetening agent Acesulfam-K Hoechst ® were dissolved in 4.9 l of the iso-maltooligosaccharide fraction, having a dry substance content of 17.2% by weight and an average molecular mass of 1250 g/mol, the fraction being obtained by chromatography on a column filled with a strongly acid cation-exchanger in the Ca++ form. By drying the solution, 840 g of a white powder, easily soluble in water, were obtained, that had a pleasantly sweet taste ("sweet" iso-malto-oligosaccharide carrier).

A strawberry jam was cooked by using

| deep frozen strawberries | 1000 g |
| "sweet"-iso-malto-oligosaccharide carrier | 500 g |
| jellying agent Opekta GB "two to one" | 25 g. |

The cooking, jellying and color characteristics were equivalent to those of a strawberry jam cooked with 500 g sucrose.

I claim:

1. A process for the manufacture of a gluco-oligosaccharide mixture having up to 30 anhydroglucose units, which comprises forming (a) an aqueous solution containing α(1→6)-D-glucosyl transferase and a mono- or di-saccharide composed of glucose units, the solution containing at least 200 mmol of the saccharide per 1000 U of transferase, and at a temperature of 265 to 310 K and a pH from 4.5 to 8 mixing solution (a) with (b) an aqueous sucrose solution in an amount such that the molar ratio of sucrose to glucose units is from 2.0 to 5.0.

2. A process according to claim 1, wherein solution (a) contains from 400 to 600 mmol of glucose per 1000 U of transferase.

3. A process according to claim 1, wherein the mixture is effected at from 290 to 300 K.

4. A process according to claim 1, wherein the pH of the mixture is from 5 to 6.5.

5. A process according to claim 1, wherein the molar ratio of sucrose to glucose units is from 3.0 to 4.0.

6. A process according to claim 1, wherein the mixture of (a) and (b) is effected continuously.

7. A process according to claim 1, wherein the mixture is effected at such a rate that the sucrose is directly converted by the transferase.

8. A process according to claim 1, wherein the mono- or di-saccharide of solution (a) is glucose.

9. A process according to claim 1, wherein the mono- or di-saccharide of solution (a) is a hydrolysed starch having a high dextrose equivalent.

10. A process according to claim 1, wherein the mono- or di-saccharide of solution (a) is maltose.

11. A process according to claim 1, wherein the dry weight of the carbohydrate content of the mixture is from 30 to 50 percent.

12. A process according to claim 1, wherein the α(1→6)-D-glucosyl transferase is the dextran sucrase produced by the bacterium Leuconostoc mesenteroides.

13. A process according to claim 1, wherein the α(1→6)-D-glucosyl transferase is the dextran sucrase produced by the bacterium Leuconostoc dextranicum.

14. A process according to claim 1, wherein the mixture is effected continuously, the mono- or di-saccharide-containing solution being added at about the same rate as it is consumed.

15. A process according to claim 1, wherein there is also mixed with (a) and (b) an antimitotic to avoid undesired yeast growth.

16. A process according to claim 15, wherein the antimitotic is sulfurous acid added in up to 1000 mg/kg.

17. A process according to claim 1, including the further step of separating from the mixture by precipitation-fractionation or chromatography the oligosaccharide produced therein.

18. In a sweetening composition comprising a calorie free carrier and a sugar substitute, the improvement which comprises employing as the carrier a product produced by the process of claim 17.

* * * * *